United States Patent [19]

Leyshon

[11] Patent Number: 4,886,932
[45] Date of Patent: Dec. 12, 1989

[54] THIN BED COFEED REACTION SYSTEM FOR METHANE CONVERSION

[75] Inventor: David W. Leyshon, West Chester, Pa.

[73] Assignee: Atlantic Richfield Company, Los Angeles, Calif.

[21] Appl. No.: 179,614

[22] Filed: Apr. 11, 1988

Related U.S. Application Data

[63] Continuation-in-part of Ser. No. 31,496, Mar. 30, 1987, which is a continuation-in-part of Ser. No. 158,128, Mar. 4, 1988.

[51] Int. Cl.$^4$ .................................... C07C 2/00
[52] U.S. Cl. .................................. 585/500; 585/654; 585/656; 585/910
[58] Field of Search .............. 585/500, 910, 911, 301, 585/654, 656

[56] References Cited

U.S. PATENT DOCUMENTS 4,672,145  6/1987  Kolts ............................. 585/500 X Primary Examiner—William R. Dixon, Jr.
Assistant Examiner—James M. Hunter, Jr.
Attorney, Agent, or Firm—William C. Long

[57] ABSTRACT

The invention relates to the conversion of methane to higher hydrocarbons by reaction of methane and gaseous oxidant under adiabatic conditions in a thin bed reactor, wherein the hydrocarbon feed contains 1 to 10 wt % $C_2+$ alkanes based on methane plus $C_2+$ alkanes.

8 Claims, 1 Drawing Sheet

THIN BED COFEED REACTION SYSTEM FOR METHANE CONVERSION

RELATED APPLICATION

This application is a continuation in part of copending U.S. patent application Ser. Nos. 07/031,496 filed Mar. 30, 1987, and 07/158,128 filed Mar. 4, 1988.

BACKGROUND OF THE INVENTION

1. Field of the Invention

The present invention relates to a further improvement in the conversion of methane to higher boiling hydrocarbons using adiabatic thin bed reactors, wherein a certain amount paraffin hydrocarbon having 2 or more carbon atoms is incorporated in the feed gas.

2. Description of the Prior Art

Methane is found in large quantities in gaseous form in somewhat remote regions of the world. The transportation of this methane to areas where it can be utilized is relatively inefficient.

Considerable work has been carried out relating to the conversion of methane to higher hydrocarbons which are readily condensable and which can be conveniently transported in liquid form. In this regard, reference is made to the following U.S. patents which are concerned with conversion of methane to higher hydrocarbons: U.S. Pat. Nos. 4,443,649; 4,444,984, 4,443,648, 4,443,645; 4,443,647; 4,443,644; 4,443,646; 4,499,323; 4,499,324; 4,593,139; 4,489,215; 4,499,322; 4,495,374; 4,544,784; 4,544,785; 4,547,610; 4,547,611; 4,517,398; 4,544,787; 4,547,608; 4,544,786; 4,568,785; 4,523,049; 4,523,050 and the like.

The conversion of methane to higher hydrocarbons in the presence of solids which may contain oxidative synthesizing agents as described in the above patents takes place effectively at elevated temperatures in the range of about 500° C. to 1200° C. The reaction is strongly exothermic in nature, and in order to properly regulate the reaction and prevent excessive undesirable side reactions, it is necessary to remove the exothermic heat of reaction to avoid an exessive temperature rise, and to rapidly lower the temperature of the reaction product mixture.

Problems particular to this conversion of methane include the fact that the reaction temperature is high enough to preclude or bring into serious question the use of many materials normally used in reactor construction.

The high temperatures result in rapid conversion of the reaction products to undesirable materials unless the residence time of the products at elevated temperatures is very short. Thus, high reaction space velocities and rapid quenching of the product are desirable.

Fixed bed reactors of the tubular or massive bed configuration have been considered for the reaction However, such systems have not been satisfactory due to their cost and complexity, to pressure drop and materials of construction problems and to problems of heat removal and effluent quenching.

A further disadvantage of conventional fixed bed reactors is that the feed must be preheated to elevated temperatures. This requires fuel as well as an expensive ceramically lined furnace.

Copending applications Ser. Nos. 07/031,496 filed Mar. 30, 1987 and 07/158,128 filed Mar. 4, 1988 describe thin bed adiabatic systems for successfully carrying out the methane conversion. It is a feature of the present invention that enhanced flow rates in a thin bed system can be achieved.

SUMMARY OF THE INVENTION

In accordance with the present invention there is provided an improved method for continuous conversion of methane to higher hydrocarbons in the thin bed reactor set forth in copending applications Ser. Nos. 07/031,496 filed Mar. 30, 1987 and 07/158,128 filed Mar. 4, 1988 wherein there is provided in the methane feed to the reactor $C_{2}+$ alkane in amount of 1 to 10% by weight of the total hydrocarbon fed.

BRIEF DESCRIPTION OF THE DRAWINGS

Accompanying

Accompanying

DETAILED DESCRIPTION OF THE INVENTION

Figure 1:
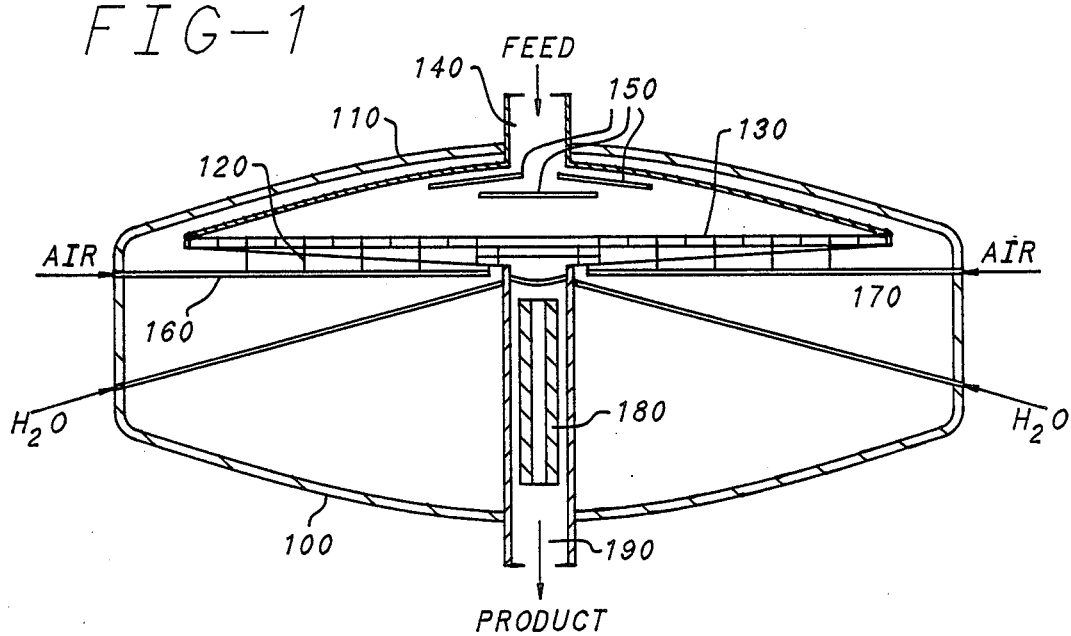
FIG. 1 illustrates in schematic form an overall reactor configuration incorporating the thin bed monolithic element.

The present invention represents a further improvement in the thin bed cofeed conversion of methane described in copending application Ser. Nos. 07/031,496 filed Mar. 30, 1987 and 07/158,128filed Mar. 4, 1988, the entire disclosure of which are incorporated herein by reference.

In said thin bed cofeed system, feed rates are limited by the heat transfer characteristics of the system. If the feed rate is too high, feed gases will not be preheated to a sufficient temperature to sustain the reaction. In addition, the heat released by reaction is proportional to the feed rate but the heat transfer rates are nearly independent of the feed rate. Thus, with adequate gas preheat, higher feed rates result in excessive catalyst temperatures, causing catalyst damage and lower yields Reducing the feed rate alleviates these problems but increases the size and cost of the commercial reactor.

In accordance with the improvement of the present invention, increased reactor throughput is achieved by incorporating in the hydrocarbon component of the feed 1 to 10 wt % of $C_{2}+$ alkanes. At the methane conversion conditions, and especially at the catalyst hot spot zone, the $C_{2}+$ alkanes undergo a cracking reaction which is endothermic in nature thus balancing to a significant extent the exothermic heat of the methane conversion. This in turn, both moderates hot spot temperature and reduces the requirement for heat removal via convection and conduction. The net effect is that significantly higher gas feed rates can be sustained in the thin bed system while maintaining stable, balanced operations.

Further, the addition of 1 to 10 wt % of $C_{2}+$ alkanes provides a beneficial effect on the selectivity of the methane conversion to higher hydrocarbons at higher pressures. Generally, higher pressures have an adverse effect on selectivity, but this is substantially obviated through this use of the $C_{2}+$ alkanes in the feed.

In accordance with the present invention, a relatively cool reaction feed gas containing both methane and an oxidant is passed into contact with a contact solid which is a reducible or non reducible metal oxide in an adiabatic thin bed reactor at conditions of elevated temperature, whereby the methane reacts to form higher hydrocarbons and coproduct water.

In practice of the invention, a reaction feed gas comprised of both methane and oxidant is provided. It is a feature of the invention that in addition to methane, the hydrocarbon feedstock employed contains 1 to 10 wt % of $C_2^+$ alkanes. The feed may contain other hydrocarbon and nonhydrocarbon components but essential to the present invention is that the feed contain 1 to 10 wt % $C_2^+$ alkane on the basis of the methane plus $C_2^+$ alkane content.

In many cases natural gas can itself be used directly where the $C_2^+$ alkane content meets the above criteria. Preferably the $C_2^+$ alkanes are $C_2$ to $C_4$ alkanes.

The oxidant gas preferably comprises molecular oxygen; other gases such as nitrogen and carbon oxides may be present. Oxides of nitrogen such as $N_2O$ can be employed but are more costly.

The use of certain materials such as chalcogens and halogens in the feed mixtures also seems to promote the desired reaction as does the presence of steam as set forth in copending application Ser. No. 07/014405 filed Feb. 13, 1987.

The ratio of hydrocarbon feedstock to oxidant gas is not narrowly critical to the present invention. Generally, it is desirable to keep the hydrocarbon/oxygen molar ratio high enough to avoid the formation of gaseous mixtures within the flammable region and low enough to obtain 20 to 30% methane conversion.. It is preferred to maintain the volume ratio of hydrocarbon/oxygen within the range of about 1–100:1, more preferably within the range of about 2–50:1. Hydrocarbon/air feed mixtures containing about 20 to 70 volume % hydrocarbon have been found to comprise a desirable feedstream. Further dilution of the feedstream with gases such as steam, although beneficial, is not necessary to practice of the invention.

The gas mixture fed to the reactor is at a temperature substantially below reaction temperature, i.e., at least 100° C. below reaction temperature and preferably at least 400° C. below reaction temperature. The reaction is carried out adiabatically, essentially no external heating or cooling is provided. The reaction is carried out in a thin bed, i.e., a bed of solid contact agent having a depth of less than 20 inches, preferably less than 8 inches.

An essential feature is that the configuration of the reactor bed must be such to permit effective flow of heat of reaction axially in a direction opposite the flow of reaction gases thus to preheat the relatively cool feed gases to reaction temperature in the reaction bed by transfer of the heat of reaction.

A suitable fixed reactor bed configuration is that of a monolith having a honeycomb configuration with a reducible metal oxide oxidative synthesizing agent coated on surface thereof or distributed throughout, the monolithic reactor bed being capable of transmitting heat of reaction by solids conduction axially countercurrent to the flow of reaction gases. Configurations which can also be suitably employed in this invention include packed beds of particles such as discrete spheres comprised of contact agent provided the bed height is sufficiently low and the particle size sufficiently large. Eddys and turbulence in such beds provide the effective axial heat transfer necessary to sustain the reaction.

Advantageously, in place of a single packed bed configuration, a number of tubes of high heat conducting material such as alumina, stainless steel, and the like can be bonded together and filled with the particles of the solid contact agent. In a preferred practice, however, metal such as stainless steel in the desired reactor bed thickness is used as a holder for the particles of contact agent, the contact agent being placed, for example, in holes drilled in a sheet of the metal through which reaction gases are passed.

In order to accomplish the objectives of the invention, the effective thermal conductivity of the reactor bed must be at least $1 \times 10^{-5}$ cal/sec−°C.−cm, and is preferably at least $5 \times 10^{-4}$ cal/sec−°C.−cm. The fixed reactor bed may be metallic, non-metallic, semiconducting or a combination. Suitable thermal conductivity can be insured by appropriate selection of the primary material used or where thermal conductivity is unsuitably low it can be enhanced by the provision of solid pieces of more conductive materials in the reactor bed.

The solid contact materials used in the methane conversion of this invention are of the type previously known and described for the oxidative conversion of methane to higher hydrocarbons.

Solids useful in the present invention include those characterized as "nonacidic". This descriptor is meant to refer to the main, predominant surface properties of the nonacidic solids. For example some solid bases are known to have acidic properties to some extent. See Tanabe, K., "Solid Acid and Base Catalysts." In: Catalysis Science & Technology, Vol. 2 (New York, Springer-Verlag Berlin Heidelberg, 1981). Currently preferred nonacidic solids used in the present process are characterized by negligible acidity (less than about 0.01 meg/gm) in the $H_o$ range less than about 3 3, preferably less than about 6.8. $H_o$ is the Hammett acidity parameter described on pp. 234–241 of Tanabe.

A further characteristic of preferred nonacidic solids for the present process is a relatively low surface area. Nonacidic solids having surface areas less than about 50 cm$^2$/gm are suitable, but the surface areas of preferred solids are within the range of about 0.1–10 m$^2$/gm.

In one distinct embodiment of this invention, methane and a gaseous oxidant are contacted with a non-acidic solid characterized by the substantial absence of reducible metal oxides. Characteristics of nonacidic acids preferred for this embodiment are that they be stable and substantially nonreducible under process conditions. Examples of suitable nonacidic solids include those solid bases described in Table 2 on p. 233 of Tanabe, supra. However, presently preferred nonacidic solids are metal oxides and mixed oxides. Alkaline earth oxides are particularly preferred, expecially MgO and CaO. Other suitable metal oxides are $SiO_2$, alpha-$Al_2O_3$, $La_2O_3$, $ThO_2$, $TiO_2$, and $ZrO_2$. Such materials are relatively stable under the conditions of the present process.

Alkali metal-promoted alkaline earth oxides are preferred nonacidic solids for tis embodiment. Such solids are described and exemplified in commonly-assigned U.S. patent application Ser. No. 06/738,110, filed May 24, 1985, the entire content of which is incorporated herein by reference. Halogen promotors may be employed; see commonly-assigned U.S. Pat. No. 4,634,800, the entire content of which is incorporated herein by reference.

In another distinct embodiment of this invention, methane and a gaseous oxidant are contacted with solid comprising a reducible metal oxide. While such solids are sometimes referred to as "catalysts" it will be understood that, under conditions of use, nonacidic solids comprising a reducible metal oxide act as selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at least one reducible oxide of at least one metal, which oxide when contacted with methane at synthesizing conditions (e.g., at a temperature within the range of about 500° to 1000° C.) produces higher hydrocarbon products, coproduct water, and a reduced metal oxide. The term "reducible" is used to identify those oxides of metals which are reduced under the aforesaid conditions. The term "reducible oxides of metals" includes: (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (pr) and also see commonly-assigned U.S. patent application Ser. No. 06/600,918 (Tb).

Reducible oxides of iron and ruthenium are also effective, particularly when associated with an alkali or alkaline earth component. See commonly-assigned U.S. patent application Ser. No. 06/600,730 (Fe) and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorus into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium, and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalytic materials. Boron and compounds thereof are also desirably present in the reducible metal oxide catalyst employed in the process of this invention. See commonly-assigned U.S. patent application Ser. No. 06/877,574, entire content of which is incorporated herein by reference. One class of boron-promoted compositions useful in the process of this invention comprises:
(1) at least one reducible metal oxide,
(2) at least one member of the group consisting of boron and compounds thereof, and
(3) at least one member of the group consisting of of oxides of alkaline earth metals.

A related class of catalyst compositions further comprises at least one alkali metal or compound thereof. Sodium and lithium are preferred alkali metal components.

One further, special class of catalyst compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing chalcogen-promoted, reducible metal oxides are disclosed in U.S. Pat. No. 4,544.785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry mixing can be used. Supported solids may be prepared by methods such as adsorption, impregnation, precipitation, co-precipitation, and dry-mixing. For example, compounds of Mn, Sn, In, Ge, Pb, Sb, Bi, Pr, Tb, Ce, Fe and/or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined at a temperature selected within the range of about 100° to 1200° C. Particular calcination temperatures will vary depending on the compounds employed. Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of other crystalline compounds, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, $H_2$, carbon oxides, steam, and/or inert gases such as $N_2$ and the noble gases.

In an especially preferred embodiment of the invention the reactor bed is a relatively thin monolithic honeycomb with the oxidative synthesizing agent dispersed throughout. The monolithic structure is preferably comprised of a substantially continuous ceramic material having suitable strength and thermal conductivity such as alumina, magnesia, cordierte, zirconia, zirconia-spinel, lithium aluminosilicates, and the like.

The thickness of the monolithic reactor can range from about 0.2 to about 20 inches but is preferably between 0.5 inches and 8 inches in thickness.

It is important to provide sufficient wall thickness relative to the opening dimensions such that adequate flow of the heat of reaction through the solid is maintained. Structurally the monolith should have sufficient wall thickness relative to the diameter of the passages to insure adequate structural integrity at reaction conditions while providing sufficient heat transfer capacity for effective reaction preheat and control. Generally speaking, wall thickness of the monolith cell should be at least as great as the effective diameter of the cell passages.

In especially preferred practice, the ratio of monolith cell wall thickness to diameter of the monolith cell passages should be in the range of about 0.2 to 4 and the wall thickness should be 0.24 cm or less.

As above mentioned, the thermal conductivity of the monolith should be at least $1 \times 10^{-5}$ cal/sec—°C.—cm in order that the reactor structure function effectively to preheat feed gases while at the same time moderating the reaction exotherm. Preferably the thermal conductivity is at least $5 \times 10^{-4}$ cal/sec—°C.—cm.

In an alternative embodiment, the monolith element can be replaced with an element comprised of a plurality of ceramic or metal tubes which are bonded together and which are filled with particles of the solid contact agent. This embodiment has the advantage over reactor systems where a thin bed of particles of contact agent is used without the plurality of tubes in that the tubes provide increased heat transfer throughout the bed thus facilitating adiabatic operation.

In still another and preferred embodiment, the reactor bed is comprised of a metal holder, for example, a stainless steel sheet having the desired thickness and having drilled therethrough a plurality of passages adapted to contain solid particles of the contact agent and permit passage therethrough of reaction gases.

Use of this metal holder reactor configuration is especially advantageous. Costs of forming particulate contact solid are much less than that of forming monolithic catalyst elements. The metal contact agent holder can provide the axial heat transfer necessary without a measurable selectivity penalty. Use of the metal holder relative to use of ceramics is advantageous in that the reactor is less expensive because metal can be welded and machined, unlike ceramics; reliability is improved since metals are less likely to fracture; replacement is easier because conventional disassembly techniques can be used; the thermal conductivity and heat capacity per unit volume of metals such as stainless steel are far higher than most ceramics resulting in significantly improved temperature control.

The methane and oxidant feed gas mixture is passed into contact with solid oxidative synthesizing agent in the thin bed reactor suitably without preheating. Upon contact with the reactor the feed gases are very rapidly heated by the exothermic reaction heat to elevated temperature effective for accomplishing the desired methane conversion reaction. Generally speaking, reaction temperatures in the range of 500° to 1200° C. are appropriate.

Operating temperatures for contacting the methane with the contact agent are preferably selected within the range of about 500° C. to about 1000° C.; the particular temperature selected depending upon the particular reducible metal oxide(s) employed in the contact agent. For example, reducible oxides of certain metals may require operating temperatures below the upper part of the recited range to minimize sublimation or volatilization of the metals (or compounds thereof) during the methane contact. Examples include reducible oxides of indium, germanium and bismuth (operating temperatures will preferably not exceed about 860° C.).

Operating pressures for the methane contacting step are not critical to the presently claimed invention. However, both general system pressure and partial pressure of methane have been found to affect overall results. Preferred operating pressure are within the range of about 0.1 to about 30 atmospheres. The partial pressure of methane in the reaction zone is preferably maintained within the range of about 0.3 atmosphere to about 8 atmospheres.

The space velocity of the gaseous reaction streams are similarly not critical to the presently claimed invention, but have been found to affect overall results. Preferred total gas hourly space velocities are within the range of about 2000 to 100,000 hr.$^{-1}$, more preferably within the range of about 4000 to 80,000 hr.$^{-1}$.

The effluent from the contact zone contains higher hydrocarbon products (e.g., ethylene, ethane and other light hydrocarbons), carbon oxides, water, unreacted hydrocarbon e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

FIG. 1 illustrates an overall reactor structure comprised of the thin reactor bed of the invention. Referring to FIG. 1, there is provided a commercial sized reactor having 25 foot diameter metal shell 100 with removable lid 110. Support means 120 are provided to support monolithic thin reactor bed 130 which in turn is comprised of 6 inch square pieces of monolith glued together. The bed has an overall diameter of 20 feet, an a thickness of 1.5 inches. Each 6 inch square element has 1400 holes of 0.035 inch diameter for the passage of reaction gas therethrough.

The feed gas mixture comprised of methane with 1 to 10 wt % $C_2^+$ alkanes based on alkanes plus methane, and oxidant enters via conduct 140 and is distributed by baffles 150 across the reactor bed.

The feed temperature is set by the heat of reaction, the diluent concentration and the desired outlet temperature. In any event, it is essential that the feed gases to the reactor bed be at least 100° C. cooler than the product mixture exiting the bed. Preferably this differential is at least 400° C.

The monolithic bed is comprised of 10% by weight $NaMnO_2$ dispersed throughout magnesia. In order to start the reaction there is provided air and burner means at 160 effective to bring the reactor bed up to the 500°–1200° C. reaction temperature.

Once this bed temperature has been established the reaction becomes self-sustaining as the inlet gases are preheated by heat of reaction conducted axially through the bed.

Water quench is provided via lines 170 and the product gases exit over heat recovery boiler tubes 180 and are removed through conduit 190.

It should be noted that in any of the desired practises of the invention, heating means should be provided during start up of the operation to heat the reactor bed to sufficiently high temperature that methane and oxidant will react upon introduction into the bed. Thereafter, the heating means are not employed and the reaction is sustained by the heat released by the reaction.

EXAMPLE 1

Figure 2:
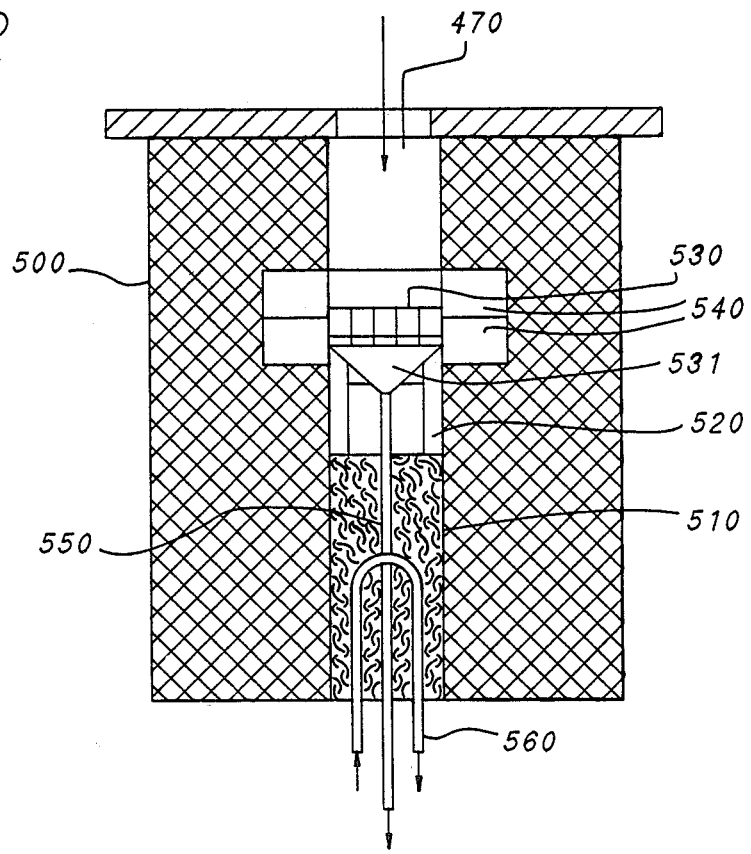
FIG. 2 illustrates in schematic form a thin bed reactor element used in the invention.

Referring to FIG. 2, there is shown a thin bed reactor containing solid catalyst particles ground to 8 to 14 mesh and placed in 6 one inch O.D. alumina tubes cemented in a bundle using Babcock and Wilcox HDHS-98 refractory.

A 10" schedule 80 pipe designated 500 is used as the reactor shell. Inside the shell is positioned a 3.5 inch O.D. 3.125 inch I.D. alumina tube 510 sealed at the bottom to isolate reaction gases from the metal shell. Ring 520 is positioned inside tube 510 to provide support for the catalyst containing tube bundle 530. Catalyst particles are maintained in the tubes by a fiberous ceramic pad resting on a funnel cast from HDHS-98 (531).

Two 1500 watt cylindrical start-up heaters 540 are provided in order to preheat the catalyst bed to reaction temperature before introduction of the methane/oxidant gas mixture. Insulation is provided in the annular space between shell 500 and alumina tube 510 which aids in supporting heater 540 and reducing heat losses.

Product tube 550 is provided for withdrawing the reaction gas product mixture. Tube 550 extends into cone 531 and at the bottom is sealed within tube 510. Water cooling coils 560 are provided to aid in quenching the reaction product mixture.

In the runs according to this example, the catalyst bed height is 2.5 inches. The catalyst is prepared as follows:

About 63.50 parts by weight MgO, 6.86 parts by weight LiOH, 17.72 parts by weight $H_3BO_3$ and 43.68 parts by weight $Mn_3O_4$ are ball milled for three hours. To the mixture is added sufficient water to form paste which is suitable for pelletizing.

After 2–3 hours drying at ambient conditions, the catalyst is calcined at 950° C. for 16 hours and then ground to 8 to 14 mesh and 70.8 grams were loaded in the tube bundle.

Feed gases enter via 570, are preheated and react in catalyst bed 530, and exit via product line 550. Thermocouples are provided (not shown) at a number of locations in the catalyst bed 530.

| | | |
|---|---|---|
| Methane | 6.5 | liters/min |
| Ethane | 0.31 | liters/min |
| Oxygen | 1.52 | liters/min |
| Steam | 4.7 | grams/min |
| $H_2S$ | 0.13 | cc/min |

The methane, ethane and oxygen flows are measured at 75° F. and 1 atm.

Initially the methane and air mixture is bypassed around the reactor and nitrogen is introduced at the rate of 100 cc/min. via 570 and passes through reactor bed 530 and into line 550 while the bed is electrically preheated by means of heater 540.

When the catalyst temperature reaches 1250° F., the reaction is commenced by diverting the bypassed hydrocarbon, steam and oxygen flows into the reactor; at this time the heaters are set to maintain adiabatic conditions. Reactor pressure is 30 psig. feed gases are at 340° F. and exit gases at 1580° F.

Carbon conversion was 23.9% and $C_2^+$ selectivity was 60.2%. Oxygen concentration in the effluent was <0.1%.

Comparative Example

By way of comparison when the above example is repeated but with no ethane in the feed, it was necessary to reduce all flows by 25% in order to achieve stable operation.

What is claimed is:

1. In a method for the oxidative conversion reaction of methane to higher hydrocarbon products and co-product water wherein a gas mixture comprising methane and a gaseous oxidant is contacted with a solid contact agent at reaction conditions in a thin adiabatic reactor bed, the improvement which comprises feeding to said reactor a gas mixture containing 1 to 10 wt %

$C_2^+$ alkanes based on the methane plus C2+ alkanes in the feed.

2. In a method for the oxidative conversion reaction of methane to higher hydrocarbon products and co-product water wherein a gas mixture comprising methane and a gaseous oxidant is contacted with a solid contact agent in a thin adiabatic reactor bed at reaction conditions, comprising the steps of:
  (1) initially heating the gas mixture to reaction temperature, causing an exothermic reaction in the thin adiabatic reactor bed;
  (2) thereafter passing the said gas mixture at a temperature at least 100° C. less than reaction temperature into said thin adiabatic reactor bed and heating the gas mixture to reaction temperature by conductive flow of heat generated by said exothermic reaction axially through said bed countercurrent to the flow of said gas mixture; and removing a reaction mixture containing said higher hydrocarbons from said bed; the improvement which comprises feeding a mixture containing 1-10 wt % $C_2^+$ alkanes based on the methane plus $C_2^+$ alkanes in the feed to said thin bed adiabatic reactor.

3. The method of claim 2 wherein the thin bed has a depth of less than 20 inches.

4. The method of claim 2 wherein the thin bed has a depth of less than 8 inches.

5. The method of claim 2 wherein the feed gases are at least 400° C. less than the reaction temperature.

6. The method of claim 2 wherein said solid contact agent is a non-acidic solid.

7. The method of claim 2 wherein said solid contact agent comprises a reducible metal oxide.

8. The method of claim 2 wherein the feed gases contain halogens or chalcogens or both.

* * * * *